US011341201B1

(12) United States Patent
Boulby

(10) Patent No.: US 11,341,201 B1
(45) Date of Patent: May 24, 2022

(54) COMPATIBILITY METHOD FOR INDIVIDUALS

(71) Applicant: Darrell Boulby, Naples, FL (US)

(72) Inventor: Darrell Boulby, Naples, FL (US)

(*) Notice: Subject to any disclaimer, the term of this patent is extended or adjusted under 35 U.S.C. 154(b) by 495 days.

(21) Appl. No.: 16/556,314

(22) Filed: Aug. 30, 2019

(51) Int. Cl.
| | | |
|---|---|---|
| *G06F 17/30* | (2006.01) | |
| *G06F 16/9536* | (2019.01) | |
| *A61B 5/16* | (2006.01) | |
| *G06F 16/683* | (2019.01) | |
| *G06Q 10/02* | (2012.01) | |
| *H04L 51/222* | (2022.01) | |
| *H04N 7/14* | (2006.01) | |
| *G06F 16/9537* | (2019.01) | |
| *A61B 5/024* | (2006.01) | |

(52) U.S. Cl.
CPC ...... *G06F 16/9536* (2019.01); *A61B 5/02438* (2013.01); *A61B 5/165* (2013.01); *G06F 16/685* (2019.01); *G06F 16/9537* (2019.01); *G06Q 10/02* (2013.01); *H04L 51/20* (2013.01); *H04N 7/141* (2013.01)

(58) Field of Classification Search
CPC ........ G06F 16/13; G06F 16/24; G06F 16/156; G06N 3/00; G06N 5/00; G05B 13/00
See application file for complete search history.

(56) References Cited

U.S. PATENT DOCUMENTS

| | | | |
|---|---|---|---|
| 2015/0088848 A1* | 3/2015 | Halt | H04L 51/10 |
| | | | 707/706 |
| 2018/0053261 A1* | 2/2018 | Hershey | G06Q 50/01 |
| 2018/0225710 A1* | 8/2018 | Kar | G06Q 30/0254 |
| 2018/0349386 A1* | 12/2018 | Circlaeys | G06F 16/48 |
| 2019/0197415 A1* | 6/2019 | Bulut | G06N 20/00 |
| 2019/0306100 A1* | 10/2019 | Guthery | G06Q 30/0273 |
| 2019/0325866 A1* | 10/2019 | Bromand | G06F 3/167 |
| 2019/0325895 A1* | 10/2019 | Bromand | G10L 13/033 |
| 2019/0325896 A1* | 10/2019 | Bromand | G10L 15/22 |
| 2020/0137011 A1* | 4/2020 | Guthery | G06F 3/04842 |

\* cited by examiner

*Primary Examiner* — Hung D Le
(74) *Attorney, Agent, or Firm* — Gulf Coast Intellectual Property Group

(57) ABSTRACT

A compatibility method for determining the likelihood that two individuals will be compatible wherein the method of the present invention implements a testing protocol that utilizes music. The present invention operably integrates with a music library of each user prior to implementing a testing protocol. The testing protocol incorporates a plurality of questions wherein the questions are provided to a user with an answer set for a user to select an answer therefrom. Subsequent selecting an answer, the software application of the present invention will cross-reference keywords in the answer with keywords in the lyrics of the songs within the music library of the user. The software application will then play an alternate song based on the keyword correlation of the aforementioned wherein the song initiates play prior to presenting the user with an additional question. The protocol continues with the software application determining an emotional quotient value.

20 Claims, 2 Drawing Sheets

COMPATIBILITY METHOD FOR INDIVIDUALS

FIELD OF THE INVENTION

The present invention relates generally to methods for matchmaking, more specifically but not by way of limitation, a method for identifying whether or not the probability for two individuals are compatible through utilizing a testing process that leverages a progressive series of questions and further incorporates the personal music library of the users.

BACKGROUND

As is known in the art there are numerous methods that are utilized by individuals to find a partner. Traditional methods of socializing and dating include but are not limited to social events and locations such as but not limited to restaurants. Almost all social events provide those individuals interested in finding a companion an opportunity to meet new people and potentially find an individual with which they may develop a relationship. Some individuals engage in looking for a partner with intentionality utilizing services that are designed to assist those looking for a meaningful relationship. These services include but are not limited to online dating services and other types of organizations.

Most dating services will leverage some type of profile based data that attempts to assist individuals find another individual with which they may be compatible. Conventional profile data can include but is not limited to likes and dislikes, hobbies and future objectives. While the aforementioned can be useful to determine the compatibility of two individuals, these conventional methods can still fall short of identifying an individual for a person that has a high probability of developing into a successful relationship. Conventional methods are deficient in areas such as but not limited to identifying the emotional intelligence and quotient as a result of using the aforementioned profile based data.

Accordingly, there is a need for a compatibility method that leverages emotional intelligence to measure the emotional quotient of an individual through implementation of a testing process wherein the testing process includes a progressive set of questions and further incorporates the personal music library of the individual.

SUMMARY OF THE INVENTION

It is the object of the present invention to provide a method for determining if two individuals have a high probability of being compatible wherein the method of the present invention incorporates a series of testing questions.

Another object of the present invention is to provide a matchmaking method operable to identify individuals that will have a high probability of developing a successful relationship wherein the series of testing questions has a progressive level of difficulty.

A further object of the present invention is to provide a method for determining if two individuals have a high probability of being compatible wherein the testing questions of the present invention have answers provided thereto.

Still another object of the present invention is to provide a matchmaking method operable to identify individuals that will have a high probability of developing a successful relationship wherein a user must select an answer from the provided answers for each of the testing questions.

An additional object of the present invention is to provide a method for determining if two individuals have a high probability of being compatible wherein the program of the present invention is operably coupled to the personal music library of the individual during the testing process.

Yet a further object of the present invention is to provide a matchmaking method operable to identify individuals that will have a high probability of developing a successful relationship wherein the program of the present invention will cross reference keywords from the selected test answer to keywords in the lyrics of the songs in the personal music library.

Another object of the present invention is to provide a method for determining if two individuals have a high probability of being compatible wherein the program establishes a database of keywords for each user wherein the keywords identify an emotional quotient for the user.

Still a further object of the present invention is to provide a matchmaking method operable to identify individuals that will have a high probability of developing a successful relationship wherein the application of the present invention identifies a likelihood of a match between two individuals based on their keyword database.

An additional object of the present invention is to provide a method for determining if two individuals have a high probability of being compatible wherein the application of the present invention will play at least one song from the personal music library ensuing a user answering a test question.

Still and additional object of the present invention is to provide a matchmaking method operable to identify individuals that will have a high probability of developing a successful relationship wherein the software application of the present invention will provide notifications to users subsequent determination of a likelihood of compatibility.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
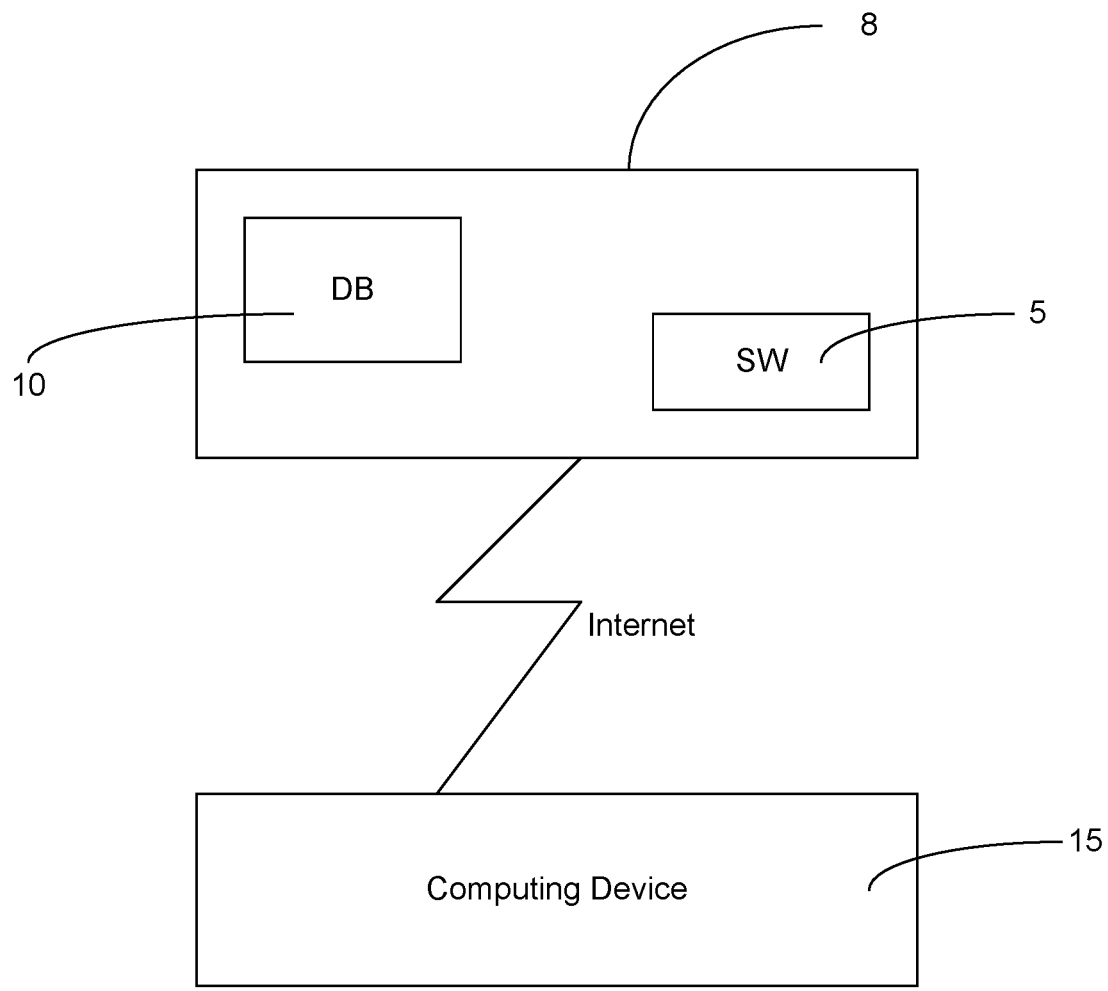
FIG. 1 is a schematic diagram of the components of the present invention.

Referring now to the drawings submitted herewith, wherein various elements depicted therein are not necessarily drawn to scale and wherein through the views and figures like elements are referenced with identical reference numerals, there is illustrated a compatibility method 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring now in particular to the drawings submitted herewith, the compatibility method 100 is a software application 5 that is loaded onto a conventional database 10 wherein the database is stored in a computing device 8 having the necessary electronics to receive, store, manipulate data. The computing device 8 is communicably coupled to the Internet utilizing convention communication protocols. A user of the compatibility method 100 will download the software application 5 onto a remote computing device 15 such as but not limited to a smart phone. It should be understood within the scope of the present invention that while only one remote computing device 15 is illustrated herein that numerous remote computing devices are operably coupled to the computing device 8 so as to access the software application 5 in order to utilize the compatibility method 100 facilitated thereby.

Figure 2:
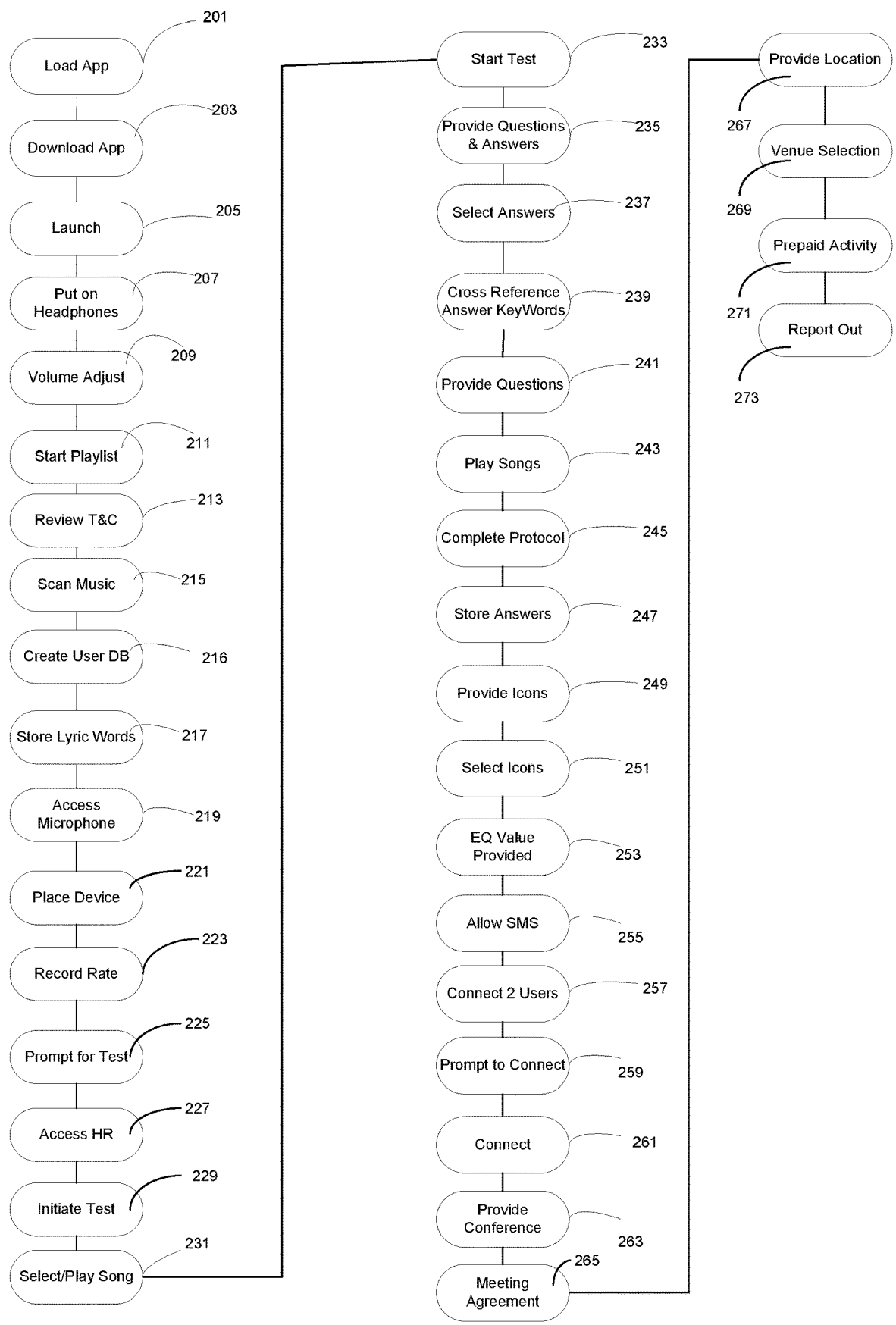
FIG. 2 is a flowchart of the process facilitated by the present invention.

Referring in particular to FIG. 2 submitted herewith, the compatibility method 100 is comprised of the following process. In step 201, the software application 5 is loaded onto the computing device 8 and made available for downloading thereof. Step 203, a plurality of users proceed to download the software application onto their remote computing devices 15. While the compatibility method 100 can be implemented utilizing various computing devices, it is contemplated within the scope of the present invention that the compatibility method 100 is engaged by users with a smart phone having audio playing capabilities. In step 205, a user will initiate the software application of the present invention. Ensuing launching the software application the user is prompted to place headphones or similar audio playing devices into or on their ears in step 207. Step 209, the user is requested to place the volume of their audio output of the smartphone at approximately fifty percent of the audio output capacity. In step 211, the user is prompted to initiate playing of either a playlist or the music library stored in their smartphone. Step 213, the user will be presented with the terms and conditions of use of the software application of the present invention and will be required to accept in order to proceed with utilization thereof. It is contemplated within the scope of the present invention that the terms and conditions of the compatibility method 100 could include but are not limited to sharing of data with various law enforcement agencies if deemed appropriate.

In step 215, the software application will scan all songs, in particular execute word/lyric verification for each song, in either the playlist and/or library for which the user provided access thereto. Step 216, a user specific database is created wherein the words/lyrics of the scanned songs are stored therein for step 217. It is contemplated within the scope of the present invention that during the creation of the user specific database the software application will eliminate certain words such as but not limited to conjunctions and prepositions. Elimination of the aforementioned word types are to create a user specific database of words/lyrics that is focused on words/lyrics having a definition and/or an associated meaning. The software application of the present invention provides a ranking and/or category to each word/lyrics stored in the user specific database. The ranking and/or categorization of the words/lyrics is configured to prioritize words and/or lyrics based on their emotional quotient. Emotional quotient is defined herein as a strength of meaning of the word. By way of example but not limitation, the word love would have a higher emotional quotient than the word like. The ranking and/or categorization of the words and/or lyrics by emotional quotient facilitates an ability the software application of the present invention to determine which words will most likely precipitate a stronger reaction and/or engagement by a user.

In step 219, the user will provide access to the microphone of their remote computing device. Step 221, the user is prompted to place their smartphone adjacent to their heart wherein the microphone is in its most proximate position. In step 223, the software application of the present invention records the heart rate of the user and stores in the user specific database. The aforementioned is a baseline heart rate, which will be subsequently utilized during the testing protocol of the present invention. Step 225, the user will be prompted to initiate the testing protocol of the present invention. In step 227, the software application of the present invention will request access to measure the heart rate of the user during administration of the testing protocol. Step 229, the software application will provide notification to the user that the testing protocol is about to commence. In step 231, the software application will select at least one song from the music library and/or playlist of the user and initiate playing thereof. Step 233, the testing protocol is commenced. In step 235, the user is provided a question and a list of answers thereto to select one choice therefrom. It is contemplated within the scope of the present invention that the testing protocol provides twenty seven answers to each question of the testing protocol. The user will review the provided answers to the questions and select an answer based on personal choice and/or preference as to which provided answer they feel best answers the question. While in the preferred embodiment of the present invention there are twenty seven provided answers to each question, it is contemplated within the scope of the present invention that an alternate quantity of answers could be provided to the test questions of the testing protocol. Step 237, the user will select an answer. In a preferred embodiment of the present invention, the software application provides an icon adjacent to each provided answer wherein the user will engage the icon to select the answer. While no particular icon is needed, it is contemplated within the scope of the present invention that the icon is an animated bug.

In step 239, the software application will cross reference keywords present in the selected answer with the words and/or lyrics of the songs in the user specific database. Step 241, ensuing completion of answering the first question the user is then provided a second question. In step 243, the software application will initiate playing of at least one alternate song wherein the song has been selected from the user's library and/or playlist. It should be understood within the scope of the present invention that more than one song could be played during the process of answering a question dependent upon the length of time the user takes to answer the question. The song selected for play in step 243 is based on the cross reference of keywords from the answer selected to the question. The software application will select a song that has the highest correlation of words in the song with the keywords from the selected answer. The objective for song selection based on the aforementioned technique is to control and/or direct the mood of the user during the test taking process. As is known in the art, music triggers an emotional response and as such the playing of a song will result in a mood development and/or change of the user during the test taking protocol. The aforementioned is further validated through comparison of the heart rate of the individual during the testing protocol with the baseline heart rate protocol previously recorded and stored for the user.

In step 245, the user will complete the testing protocol wherein each test question provided is additionally provided with twenty seven answers for the user to select therefrom. While no particular quantity of questions are required, in the preferred embodiment of the present invention it is desirable for nine questions with answer sets to be provided to a user during the testing protocol. As described previously herein, for each question provided the software application will select a song from the music playlist and/or library of the present invention wherein the song selection is based on the correlation of words with the keywords from the selected answer. In the preferred embodiment of the present invention the user will be provided with nine questions and as such nine songs will be played during the testing protocol. It is further contemplated within the scope of the present invention that the testing protocol has a time limit. While no particular time limit is required, good results have been achieved providing a time limit of seven hours and twenty nine minutes.

In step 247, the selected answers from the testing protocol are assembled and stored in the user specific database wherein a final keyword analysis is done thereon and an emotional quotient for the user is established. Step 249, upon completion of the testing protocol the user is provided with a multitude of icons wherein a user will select an icon in order to provide a preferred graphical representation of the user within the software application. In the preferred embodiment of the present invention the multitude of icons are animated bugs. In step 251, the user will select an icon from the provided multitude of icons. Step 253, the user is provided with their emotional quotient value wherein the value is determined from the keywords and cross-referenced words in the music library. In step 255, the user is prompted with an approval to accept text messaging wherein the text messaging takes place intermediate the users of the compatibility method 100 and is executed within the software application of the present invention. It is contemplated within the scope of the present invention that the software application of the present invention would monitor the text messages intermediate the users and if threatening or similar keywords are detected the software application of the present invention will provide notification to the appropriate legal authorities.

In step 257, the software application will cross reference the emotional quotient value of the users and identify two users that have either the same or similar emotional quotient value based on the results from the testing protocol. Step 259, the software application of the present invention provides a prompt to two users for a potential opportunity to connect through the compatibility method 100. In step 261, the two users agree to connect through the software application. Step 263, ensuing agreement by two users to connect, the software application will facilitate a virtual meeting between the two users. While the virtual meeting can be conducted utilizing audio and/or video, in the preferred embodiment of the present invention the virtual meeting is conducted via video conference. It should be understood that the video conference is conducted within the software application of the present invention. It is further contemplated within the scope of the present invention that the software application of the present invention provides a time limit to the video conference. In step 265 subsequent the video conference between the two users, the two users can agree to meet in person. Step 267, the software application of the present invention will identify and/or confirm the geo-location of each of the two users. In step 269, the software application will select a venue such as but not limited to a restaurant wherein the venue will function as the meeting place for the two users to meet. Step 271, the two users will meet at the designated venue and will engage in an activity that has been pre-paid by the operator of the present invention. By way of example but not limitation, if the venue is a restaurant, a pre-paid meal for two is provided to the two users. In step 273, subsequent the in-person meeting each of the users will complete a questionnaire about the in-person meeting with the other user. Data from this report will be utilized to perform activities such as but not limited to validation and verification of the establishment of an emotional quotient value utilizing the methodology of the present invention.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method for determining compatibility of at least two individuals in order to potentially establish a relationship therebetween comprising the steps of:

providing a software application, said software application being stored on a computing device wherein the computing device is accessible via conventional communication protocols;

downloading the software application, wherein users download the software application onto a remote computing device;

registering with the software application, wherein the users will complete the registration process of the software application;

accessing a music library of the users, wherein the software application will access the music library of the users;

scanning the lyrics of songs in the music library, wherein the software application of the present invention scans the songs and identifies keywords therein;

presenting at least one test question, wherein the at least one test question is presented in conjunction with answers from which to choose and comprises the testing protocol, wherein the at least one test question is further presented while simultaneously playing at least one song from the music library;

answering the at least one test question, wherein the user will select from one of the answers provided with the at least one test question;

establishing an emotional quotient value for the user, wherein the emotional quotient value is based on keywords identified in the selected answer and keywords in the music library;

identifying a potential match, wherein the software application will identify another individual that could be a match based on equivalent emotional quotient values.

2. The method for determining compatibility of at least two individuals as recited in claim 1, and further including the step of establishing a baseline heart rate, wherein a baseline heart rate is measured and recorded prior to test implementation.

3. The method for determining compatibility of at least two individuals as recited in claim 2, and further including step of playing an additional song, wherein the additional song is selected by the software application of the present invention.

4. The method for determining compatibility of at least two individuals as recited in claim 3, wherein the additional song is selected utilizing a cross reference of keywords from the selected answer and the words of the song.

5. The method for determining compatibility of at least two individuals as recited in claim 4, and further including the step of providing a time limit to complete the testing protocol.

6. The method for determining compatibility of at least two individuals as recited in claim 5, and further including establishing communication between two users of the software application, wherein the two users have been identified as having a generally equivalent emotional quotient value.

7. The method for determining compatibility of at least two individuals as recited in claim 6, and further including the step of providing a pre-paid activity for two users wherein the two users have agreed to meet.

8. A method for determining compatibility of two individuals in order to potentially establish a relationship therebetween comprising the steps of:

providing a software application, said software application being stored on a computing device wherein the computing device is accessible via conventional communication protocols;

accessing the software application, wherein users access the software application using a remote computing device and download a copy thereto;

registering with the software application, wherein the users will complete the registration process of the software application;

prompting users to access a music library stored on their remote computing devices, wherein ensuing registration the software application will request access to the music library of the users;

accessing a music library of the users, wherein the software application will access the music library of the users;

scanning the lyrics of songs in the music library, wherein the software application of the present invention scans the songs and identifies keywords therein;

establishing a user specific database, wherein the user specific database will include identified keywords from the songs in the music library;

presenting a plurality of test questions, wherein each of the plurality of test questions are presented to the users in a sequential order;

providing a group of answers for each of the plurality of test questions, wherein each test question is provided with a pre-selected answer set from which the user will choose one answer;

answering the plurality of test questions, wherein the user will answer the plurality of test questions in an order provided;

playing at least one song, wherein the software application will play at least one song for each test question presented to a user;

establishing an emotional quotient value for the user, wherein the emotional quotient value is based on keywords identified in selected answers from the answer sets and keywords in the music library;

identifying a potential match, wherein the software application will identify another individual that could be a match based on equivalent emotional quotient values.

9. The method for determining compatibility of two individuals as recited in claim 8, and further including the step of cross-referencing keywords from an answer set to the words in songs of the music library, wherein a song is identified having a strong correlation in keywords with the answer set.

10. The method for determining compatibility of two individuals as recited in claim 9, and further including the step of playing an additional song based on the correlation in keywords with the answer set, wherein the song is played while a subsequent test question is being presented to a user.

11. The method for determining compatibility of two individuals as recited in claim 10, and further including the step of providing a text message function between two users that have been identified as a potential match.

12. The method for determining compatibility of two individuals as recited in claim 11, and further including the step of providing a video conference between two users wherein the two users have agreed thereto.

13. The method for determining compatibility of two individuals as recited in claim 12, and further including the step of identifying the geo-location of each of the two users that have engaged in a video conference.

14. The method for determining compatibility of two individuals as recited in claim 13, and further including the step of locating a venue for the two users wherein the venue has been identified as a place wherein the two users who engaged in the video conference can meet.

15. A method for determining compatibility of two individuals in order to potentially establish a relationship therebetween comprising the steps of:
   providing a software application, said software application being stored on a computing device wherein the computing device is accessible via conventional communication protocols;
   accessing the software application, wherein users access the software application using a remote computing device and download a copy thereto;
   registering with the software application, wherein the users will complete the registration process of the software application;
   prompting users to access a music library stored on their remote computing devices, wherein ensuing registration the software application will request access to the music library of the users;
   accessing a music library of the users, wherein the software application will access the music library of the users;
   scanning the lyrics of songs in the music library, wherein the software application of the present invention scans the songs and identifies keywords therein;
   establishing a user specific database, wherein the user specific database will include identified keywords from the songs in the music library;
   presenting a plurality of test questions, wherein each of the plurality of test questions are presented to the users in a sequential order;
   providing a group of answers for each of the plurality of test questions, wherein each test question is provided with a pre-selected answer set from which the user will choose one answer;
   answering the plurality of test questions, wherein the user will answer the plurality of test questions in an order provided;
   cross-referencing keywords from each answer set to words in the songs of the music library, wherein a song is identified having a strong correlation in keywords with the answer set;
   selecting at least one song, wherein the at least one song is selected based on a high correlation with keywords from a previously selected answer set;
   presenting an additional test question, wherein ensuing completion of a prior test question the additional test question is provided to the user;
   playing the at least one song, wherein the software application will play the at least one song while presenting the additional test question presented to the user;
   establishing an emotional quotient value for the user, wherein the emotional quotient value is based on keywords identified in selected answers from the answer sets and keywords in the music library and a correlation of quantity amount therewith;
   identifying a potential match, wherein the software application will identify another individual that could be a match based on equivalent emotional quotient values.

16. The method for determining compatibility of two individuals as recited in claim 15, and further including the step of notifying two users of a potential match, wherein the two users have been identified based on similar emotional quotient values.

17. The method for determining compatibility of two individuals as recited in claim 16, and further including the step facilitating a first communication between the two users wherein the communication can be text or video.

18. The method for determining compatibility of two individuals as recited in claim 17, and further including the step of identifying a venue for the two users to meet ensuing the completion of the first communication.

19. The method for determining compatibility of two individuals as recited in claim 18, and further including the step of providing a pre-paid activity for the two users at the identified venue.

20. The method for determining compatibility of two individuals as recited in claim 19, and further including the step completing a report of the pre-paid activity, wherein the two users will complete a report about the pre-paid activity utilizing the software application.

* * * * *